United States Patent [19]

Pap et al.

[11] Patent Number: 5,043,163

[45] Date of Patent: Aug. 27, 1991

[54] PESTICIDE COMPOSITION

[75] Inventors: Laszlo Pap; Eva Somfai; Andras Szego, all of Budapest; Istvan Szekely, Dunakeszi; Lajos Nagy, Szentendre; György Hidasi, Budapest; Sandor Zoltan, Budapest; Andrea Toth, Budapest; Bela Bertok, Budapest; Sandor Botar, Budapest; Antal Gajary, Budapest; Agnes Hegedüs, Budapest; Aniko Deak, Budapest, all of Hungary

[73] Assignee: Chinoin Gyogyszer- es Vegyeszeti Termekek Gyara Rt., Budapest, Hungary

[21] Appl. No.: 565,881

[22] Filed: Aug. 9, 1990

Related U.S. Application Data

[63] Continuation-in-part of Ser. No. 274,231, Nov. 18, 1988.

[30] Foreign Application Priority Data

Nov. 18, 1987 [HU] Hungary .............................. 5114/87

[51] Int. Cl.$^5$ ............................................. A01N 25/00
[52] U.S. Cl. ........................................ 424/405; 514/80
[58] Field of Search ........................... 514/80; 424/405

[56] References Cited

U.S. PATENT DOCUMENTS 4,845,126 4/1983 Hidasi et al. .

FOREIGN PATENT DOCUMENTS 3219200 11/1983 Fed. Rep. of Germany .
3317399 1/1984 Fed. Rep. of Germany .
WO86/04215 7/1986 PCT Int'l Appl. .
2074867 11/1981 United Kingdom .

Primary Examiner—Lester L. Lee
Assistant Examiner—Eric J. Kraus
Attorney, Agent, or Firm—Herbert Dubno; Jonathan Myers

[57] ABSTRACT

The present invention relates to a multi-component pesticidal composition against anthropoda containing as active ingredient pyrethroides and phosphate esters and optionally piperonyl butoxide and excipients comprising as pyrethroid component 0.1 to 40 percent by weight of cypermethrin related to the total weight comprising out of the 8 possible isomers 40 to 100 percent by weight of 1RcisS and/or 1RtransS stereoisomer and as a second component at least one phosphoric acid, thiophosphoric acid or dithiophosphate being toxic on arthropoda at a ratio of 1:1-99 related to the amount of cypermethrin.

4 Claims, No Drawings

PESTICIDE COMPOSITION

This is a continuation-in-part of co-pending application Ser. No. 07/274,231 filed on Nov. 18, 1988.

FIELD OF THE INVENTION

The present invention relates to a new arthropodicide pesticide composition containing as active ingredient a special pyrethroidal combination, a phosphoric acid derivative and optionally piperonyl butoxide and/or excipients.

The present invention relates to a composition of several active ingredients against arthropoda and it contains as active ingredient pyrethroids and phosphate esters and optionally piperonyl butoxide and excipients and as a pyrethroid component it contains 0.1-40 percent by weight of cypermethrin consisting of 40-100 percent by weight of 1RcisS and/or 1RtransS stereoisomer out of the possible 8 isomers and related to the cypermethrin isomer at a ratio of 1:1-99 and at least one phosphoric acid, thiophosphoric acid or dithiophosphate being toxic against arthropoda.

BACKGROUND OF THE INVENTION

One of the obvious reasons for using mixtures of active ingredients is the different sensitivities of the individual pests to the used chemicals and it is often cheaper, simpler or more efficient to use the suitably combined mixtures on one single occasion (J. Stored Prod. Res., 1977, Vol. 13. 129-137; Pestic. Sci., 1983. 14 385-398; Pestic. Sci., 1983. 14 373-384; JP PS 50 58237(1975)1973;(54 95730) (1979/1978); 54 92625; 53 62830 (1970)1976).

It is known that the absorbed pyrethroids are made ineffective by the insects through different mechanisms. One of these detoxification methods is realized by esterases: by splitting the ester bond, the pyrethroid hydrolyzes to a non-toxic molecule. The phosphate esters inhibit certain variations of enzymes metabolizing pyrethroids.

The esterases are different with regard to species localization substrate-specific character and kinetic parameters. The inhibitor activity of certain esterase inhibitors is consequently different. Thus if on one species, an esterase inhibitor influences the metabolism of a given, pyrethroid one cannot tell the possible interaction of another species or another pyrethroid molecule.

Thus, for instance, the insecticide pro feno fos effectively inhibiting enzymes hydrolyzing permethrin, cypermethrin does not effect the activity of pyrethroids measured on Tribolium castaneum grubs (Pestic. Biochem. Physiol., 1980, 14 81-85, Pestic. Sci., 1983 14 367-372).

A further example of the contradictory results is that the insecticide chlorpyriphos acts as a synergist for flycitrinate and fenvalerate on Spodoptera littoralis but it acts as an antagonist the toxicity of cypermethrin (BCPC Proceedings Vol. 3:943). Against the same species monocrotophos, pro feno fos, azinphos-methyl and acephate act as a synergistic agent in a broad combination range together with cypermethrin, fenvalerate and deltamethrin. The following combinations are exceptions: fenvalerate+azinphos-methyl, deltamethrin-+azinphos-methyl and deltamethrin+pro feno fos double mixtures (Phytoparasitica 1986. 14/(2):101) which show an additive or antagonist interaction. The synergism could be shown only by oral administration of the active ingredients, the topical tests were without any result.

Against field resistance a successful result can be expected with those combinations where between the activity of the individual components a negative cross-correlation can be observed. One of the less thoroughly examined mixtures is the mixture of fenvalerate and azinphos-methyl and a negative cross-correlation against spider mites (Tetranychus urticae) is disclosed in Nature 1979 281:298. The 1:1 mixture of the two active ingredients resulted in a favorable activity against sensitive and resistant spider mites (Pestic.Sci., 1980 11:600).

According to the DBP 27 57 768 mixtures containing permethrin as one component and bromophosethyl, chlorpyriphos, bromphos, malathion and diazinon as a second component showed an antagonist interaction in the laboratory against the normally sensitive house fly (Musca domestica), but on harvested and resistant populations the $LD_{50}$ value which is one order of magnitude higher, showed a de facto synergism. On Christoneura occidentalis belonging to the order of Lepidoptera chlorpyriphos showed a synergistic effect with deltamethrin at a ratio of 10:1 but acted as an antagonist to permethrin and fenvalerate (J.Econ.Entomol., 1984. 77 16-22) whereas on another Lepidoptera species (Ostrinia nubialis) the combination of permethrinchlorpyriphos showed a significant synergism within a wide combination range (J.Econ.Entomol., 1982 75 28-30).

It may occur that synergism may be observed on the sensitive strain and on the already resistant strain antagonism can be observed. As an example for this effect the interaction of cypermethrin and monocrotophos on Spodoptera littoralis can be mentioned. See Med.Fac.-Landbouw.Rijksuniv.Gent, 50/2b, 1985 751.

The abbreviations used in the tables of this specification are as follows:

CIP=Cypermethrin=Alpha-cyano-3-phenoxybenzyl-3-(2,2-dichlorovinyl)-2,2-dimethyl-cyclopropane-carboxylate CHX="chinmix"=out of the possible isomers of cypermethrin a 40:60 mixture of 1RcisS+1ScisR:1RtransS+1StransR isomers TRX=transmix=out of the possible isomers of cypermethrin a 50:50 mixture of 1RtransS:1StransR isomers QUI=quinalphos=0,0-diethyl-0-quinoxalin-2-yl phosphorothioate DIA=diazinon=0,0-diethyl-0-2isopropyl-6-methyl-pyrimidine-4-yl-phosphorothioate TRIA=triazophos=0,0-diethyl-0-1-phenyl-1H-1,2,4-triazole-3-yl-phosphorthioate MET=methidathion=S-2,3-dihydro-5-methoxy-2-oxo-1,3,4-thiadiazol-3-yl-methyl-0,0-dimethyl-phosphorodithioate HEPT=heptenophos=chlorobicyclo3,2,0hepta-2,6-dien-6-yl-dimethyl-phosphate PHOS=phosalone=S-6-chlor-2,3-dihydro-2-oxobenzoxazol-3-yl-methyl 0,0-diethyl-phosphorodithioate SF=synergistic factor PBO=piperonyl-butoxide

SUMMARY OF THE INVENTION

Our invention is based on the recognition that by using determined stereoisomers or mixtures thereof of cypermethrin active ingredient the interaction's direction and extent is considerably determined by the steric structure of the tested cypermethrin. It has been found that by maintaining the combination ratio unchanged.

the same mixture has all the forms of interactions such as synergism, additivity or antagonism depending on which stereoisomer of cypermethrin is used.

No publication is known relating to pyrethroid+-phosphate ester compositions in which the interaction of the pyrethroid combination had been examined with all possible isomers. Our experiments are shown in Examples 1 to 4.

Example 1 demonstrates the interactions of three cypermethrin isomers and quinalphos on Musca domestica at a combination rate of 1 to 5. Depending on the used isomer antagonist, additive and synergistic interactions can all be observed.

By changing the ratio of cypermethrin isomer:phosphate ester to 1:10 the four separately tested isomers act as a synergistic agent with quinalphos (see Table 2). Similar tendency can be observed when testing chinmix containing 4 isomers with quinalphos: by increasing the partial ratio of phosphate ester the antagonism is converted to additivity and starting from the partial ratio 1:10 it turns to synergism. The cypermethrin containing 8 isomers behaves quite differently showing an antagonistic action at the ratio of 1:10 and 1:20 (Example 2). Some isomer mixtures of cypermethrin containing 8 isomers show different interactions when combined with various insecticides and acaricides. By testing the individual cases we have shown that in the case of certain cypermethrin isomers excellent synergistic effects can be obtained by the favorable choice of the combination ratios when compared with cypermethrin containing 8 isomers. According to our tests especially those combinations give favorable results in which the cypermethrin component consists of at least 40% 1RcisS and/or 1RtransS isomers.

On the basis of data of Example 2 the following table can be set up:

phoric acids. Some examples are given below by their E-ISO names without their complete chemical names:

phosphoric acids: phosphamidon, heptenophos, tetrachlorvinphos, dichlorvos, trichlorphon, propetamphos thiophosphoric acids: parathion, methylparathion, fenitrothion, diazinon, triazophos, pirimiphos-ethyl, pirimiphos-methyl, demeton, mevinphos, quinalphos, fenthion, bromophos, coumaphos, ethoprop, cyanophos dithiophosphates: malathion, mephospholan, phormothion, phenthoate, phosmet, methidathion, phosalone, sulprofos.

Particularly preferred thiophosphoric acids are selected from quinalphos, diazinon, triazophos and dithiophosphates are preferably selected from phosalone and methidathion and preferred phosphoric acid is heptenophos.

The advantage of the new composition is that a significant synergistic interaction can be achieved without changing of the activity and a dose reduction can be obtained relative to the totally used active ingredient. Thereby the burden of environment and the costs of plant protection can be reduced relative to other combinations of phosphate esters containing cypermethrins comprising all isomers.

The favorable effect can be explained by the different activity mechanism of the components of the mixture. The highly lipid soluble cypermethrin isomers which act rapidly on contact are; less selective and kill all arthropoda to be found in the treated field, as opposed to phosphate esters which kill first of all pests consuming the treated crop as nourishment, so that their activity against the useful arthropoda is lower. The cypermethrin dose can be considerably reduced in the composition of the invention due to the synergistic effect

| | QUINALPHOS-COMBINATIONS | | | | | |
|---|---|---|---|---|---|---|
| cypermethrin isomer mixtures | number of isomers | cis:trans ratio | 1RcisS + 1RtransS: ratio of other isomers | LD$_{50}$/ng/fly | | |
| | | | | alone | −Qui | SF |
| cypermethrin | 8 | 40:60 | 25:75 | 11.0 | 14.1 | 0.78 |
| transmix | 2 | 0:100 | 50:50 | 9.4 | 7.1 | 1.32 |
| chinmix | 4 | 40:60 | 50:50 | 4.6 | 3.6 | 1.31 |
| 1RcisS + 1RtransS | 2 | 50:50 | 100:0 | 2.3 | 1.6 | 1.44 |

Accordingly the compositions of the invention comprise of a given cypermethrin isomer mixture and as organic phosphate ester insecticide and optionally an activator serving for the killing of arthropoda, for the inhibition of their development and propagation, for disturbing their behavior and nourishment and finally for preventing their damaging activity. As a pyrethroid the combination comprises cypermethrin containing at least 40% of 1RcisS and 1RtransS isomer, preferably at a ratio of 1RcisS:1ScisR:1RtransS:1StransR=20:20:30:-30-40:40:10:10 and 1RtransS:1StransR=40-60-100:0.

The combination ratio of cypermethrin isomer and phosphate ester in the composition can vary between 1:1 and 1:99 preferably between 1:10-1:99 preferably between 1:10-1:99, more preferably 1:10 to 1:40, especially 1:10 to 1:30, and most preferably 1:10 to 1:25.

The composition of the present invention contains as phosphate ester insecticides and acaricides preferably phosphoric acids, thiophosphoric acids and dithiophosalthough the phosphate ester dose is sublethal per se, the unfavorable side effect of the pyrethroids on the useful parasites is reduced. As a whole the sublethal phosphate ester doses show a lower toxic effect on the useful arthropoda as they are not subject to oral poisoning or only indirectly.

According to the present invention such combinations are preferred for use against agricultural pests which contain as cypermethrin active ingredient 1RcisS+1ScisR:1RtransS+1StransR enanthiomer pairs at a ratio of 55:45-25:75. It is further preferred if this composition contains 5-50 percent by weight of quinalphos, diazinon and/or phosalone and 0-10 percent by weight of piperonyl-butoxide. In these cases emulsifiable concentrates are preferred containing as one carrier an aromatic solvent mixture, preferably alkyl benzenes, such as Solvesso 100, Solvesso 150.

Another preferred field of application of the composition according to the invention is the veterinary field. These compositions contain preferably 1RtransS and 1StransR enanthiomer pair, 5-50 percent by weight of phosalon or 5-50 percent by weight of malathion and 0-10 percent by weight of piperonyl-butoxide. The veterinary compositions are preferably emulsified concentrates containing as excipient an aromatic solvent mixture, preferably alkyl benzenes at a ratio of 1:0.2-10 related to the weight of the total active ingredient.

The compositions can contain ionic surfactants as excipients, preferably 0.1-20 percent by weight of a calcium salt of alkyl-aryl-sulphonate, non-ionic-surfactants preferably 0.5-40 percent by weight of alkylphenolpolyglycolether containing 10 moles of ethylene oxide and/or 0.5-40 percent by weight of tristiryl phenolethoxylates (EO=20) and solvents preferably xylene or aromatic solvent mixtures.

Emulsifiable concentrates of good quality can be obtained in the case of quinalphos or optionally quinalphos PBO combinations in aromatic solvent mixtures. In some cases special aromatic solvent mixtures can be preferred. As a surfactant 10-40 g/l calcium salt of alkyl-aryl-sulphonate is preferred and as a non-ionic surfactant 50-100 g/l alkylphenolpolyglycol esters containing 10 mole of ethylene oxide and/or 10-100 g/l tristirylphenol ethoxylates (EO=20) are preferred. For phosalone combinations xylene can be replaced by an aromatic solvent mixture or special aromatic solvents such as Solvesso 100-150.

Transparent solutions can be obtained if the active ingredient is dissolved in xylene or in aromatic solvent mixtures and as a cosolvent n-butanol may be used. For the preparation of a water soluble transparent solution the combination of the surfactants used for emulsifiable concentrates can be used but the concentration is increased to 20-50 percent by weight.

As an aromatic solvent mixture such mixtures are preferred which are prepared by catalytic aromatization of benzene wherein the minimal aromatic part amount to 75% and substantially pure aromatic hydrocarbon fractions are obtained. A preferred product is as follows:

Solvesso 100 (99% of aromatic content, 90% of $C_9$-alkyl-benzene)
Solvesso 150 (99% of aromatic content, 85% of $C_{10}$-alkyl-benzene).

Shellsol A, Aromasil H and Aromatol are also suitable.
The details of the invention are illustrated in the following examples:

EXAMPLE 1

The efficiency of the insecticides and insecticidal mixtures was determined on 3-5 days old female house flys (Musca domestica) imagoes grown in the laboratory. The active ingredient amount was applied in 0.22 $\mu l$ drops on the dorsal cuticle of flies moderately narcotized with $CO_2$. As a solvent n-butanol or 2-ethoxy ethanol was used. The treated flies were placed into plexi glass containers and they were supplied with sugar and water ad libitum. After 24 hours the number of killed flies were calculated and their ratio was expressed in percents. For each dose 20 flies were examined in 2-4 parallel tests. The tests were repeated on 3-5 various occasions.

The combined interaction is given according to the ratio of the expected effect calculated on the basis of the activity of the components per se to the measured effect. If the measured effect is higher than the expected effect then the interaction is synergistic, if the two effects are the same then it is additive and if the effect is lower then there is an antagonistic effect in the components. In the examples the difference of the expected and measured effects for each dose in percents is given by the cotoxicity index. According to the above the positive value shows a synergistic, and the negative value an antagonistic activity.

TABLE 1

Interaction of cypermethrin isomers and quinalphos measured by topical method on house fly (Musca domestica)
Ratio of pyrethroid and phosphate ester = 1:5

| dose (ng × $fly^{-1}$) | | measured effect (%) | | | expected effect (%) | cotoxicity index (%) |
|---|---|---|---|---|---|---|
| 1RtransS 1:5 | QUI[x] | 1RtansS | QUI | 1RtransS − Q | | |
| | | mortality | | | | |
| 0.93 | 5 | 0 | 0 | 0 | 0 | — |
| 1.56 | 8 | 0 | 0 | 0 | 0 | — |
| 2.59 | 13 | 20 | 0 | 15 | 20 | −5 |
| 4.32 | 22 | 30 | 0 | 30 | 30 | 0 |
| 7.20 | 36 | 65 | 0 | 60 | 65 | −5 |
| 12.00 | 60 | 90 | 0 | 90 | 90 | 0 |
| 1RcisS 1:5 | QUI | 1RcisS | QUI | 1RcisS + QUI | | |
| 0.35 | 2 | 0 | 0 | 0 | 0 | 0 |
| 0.50 | 3 | 5 | 0 | 10 | 5 | +5 |
| 0.72 | 4 | 15 | 0 | 25 | 15 | +10 |
| 1.03 | 5 | 35 | 0 | 40 | 35 | +5 |
| 1.47 | 7 | 45 | 0 | 60 | 45 | +15 |
| 2.10 | 11 | 70 | 0 | 75 | 70 | +5 |
| 3.0 | 15 | 90 | 0 | 100 | 90 | +10 |
| 1StransR | QUI | 1StransR | QUI | 1StransR + QUI | | |
| 48 | 240 | 0 | 15 | 0 | 15 | −15 |
| 67 | 343 | 0 | 25 | 10 | 25 | −15 |
| 98 | 490 | 0 | 45 | 25 | 45 | −20 |
| 140 | 700 | 0 | 60 | 40 | 60 | −20 |
| 200 | 1000 | 10 | 75 | 65 | 85 | −20 |

[x]Quinalphos doses were made round to an integer.

TABLE 2

Interaction of cypermethrin isomers and quinalphos on house fly (*Musca domestica*) measured by topical method
Ratio of pyrethroid and phosphate ester: 1:10

| dose (ng × fly$^{-1}$) | | measured effect (%) | | | expected effect (%) | cotoxicity index (%) |
|---|---|---|---|---|---|---|
| 1RtransS | QUI 1:10 | 1RtransS | QUI | 1RtransS + Q | | |
| | | | mortality | | | |
| 1.56 | 17 | 0 | 0 | 10 | 0 | +10 |
| 2.59 | 26 | 20 | 0 | 40 | 20 | +20 |
| 4.32 | 43 | 30 | 0 | 70 | 30 | +40 |
| 7.20 | 72 | 65 | 0 | 90 | 65 | +25 |
| 12.00 | 120 | 90 | 0 | 100 | 90 | +10 |
| 1RcisS | QUI 1:10 | 1RcisS | QUI | 1RcisS + QUI | | |
| 0.35 | 4 | 0 | 0 | 5 | 0 | +5 |
| 0.50 | 5 | 5 | 0 | 25 | 5 | +20 |
| 0.72 | 7 | 15 | 0 | 35 | 15 | +20 |
| 1.03 | 10 | 35 | 0 | 50 | 35 | +15 |
| 1.47 | 15 | 45 | 0 | 75 | 45 | +30 |
| 2.10 | 21 | 70 | 0 | 85 | 70 | +15 |
| 3.00 | 30 | 90 | 0 | 100 | 90 | +10 |
| 1StransR | QUI 1:10 | 1StransR | QUI | 1StransR + QUI | | |
| 11.8 | 118 | 0 | 0 | 10 | 0 | −10 |
| 16.8 | 168 | 0 | 0 | 20 | 0 | +20 |
| 24.0 | 240 | 0 | 15 | 35 | 15 | +20 |
| 34.3 | 343 | 0 | 25 | 55 | 25 | +30 |
| 49.0 | 490 | 0 | 45 | 70 | 45 | +25 |
| 70.0 | 700 | 0 | 60 | 80 | 60 | +30 |
| 100.0 | 1000 | 0 | 75 | 100 | 75 | +25 |
| 1ScisR | QUI 1:10 | 1ScisR | QUI | 1ScisR + QUI | | |
| 11.8 | 118 | 0 | 0 | 15 | 0 | −15 |
| 16.8 | 168 | 0 | 0 | 25 | 0 | +25 |
| 24.0 | 240 | 0 | 15 | 40 | 15 | −25 |
| 34.3 | 343 | 0 | 25 | 60 | 25 | +35 |
| 49.0 | 490 | 0 | 45 | 75 | 45 | +30 |
| 70.0 | 700 | 0 | 60 | 90 | 60 | +30 |
| 100.0 | 1000 | 0 | 75 | 100 | 75 | +25 |

The data of Table 1 show that the certain pure isomers of cypermethrin show a different interaction with quinalphos at an unchanged combination ratio of 1:5 depending on the doses. Additivity (1RtransS), antagonism (1StransR) and synergism (1RcisS) can be observed independently of the cis:trans ratio or of the staric structure of the 1C- and alphac-asymmetric carbon atoms.

Table 2 shows synergism for the combination of various cypermethrin isomers with quinalphos at a ratio of 1:10 whereas at a ratio of 1:5 all forms of the interactions occur (Table 1).

EXAMPLE 2

The interaction of cypermethrin, chinmix, transmix and 1RcisS+1RtransS (1:1) cypermethrin isomer mixture with quinalphos are examined by using methods disclosed in Example 1. The results are summarised in Table 3 and the results demonstrate well that as opposed to the pure cypermethrin isomers chinmix, transmix and the 1:1 mixtures of 1RcisS+1RtransS show a significant synergism at a ratio of 1:10 or higher of pyrethroid:phosphate ester.

The mixtures of cypermethrin consisting of 8 isomers: quinalphos at a ratio of 1:10–1:20 show antagonism.

As the doses of quinalphos in 1:10 mixtures would be per se ineffective the extent of the synergistic interaction can be obtained if the LD$_{50}$ values measured alone in cypermethrin isomer mixtures are divided by LD$_{50}$ values measured in the combination. The Table 4 shows the values calculated from the data of Table 3 by probit analysis (Finney 1971).

TABLE 4

Interaction of cypermethrin isomer mixtures and quinalphos on house fly (*Musca domestica*) measured by topical method.
Ratio of pyrethroid and quinalphos: 1:10

| cypermethrin isomer mixtures | alone | | in combination | | synergistic factor | |
|---|---|---|---|---|---|---|
| | LD$_{50}$ | LD$_{95}$ | LD$_{50}$ | LD$_{95}$ | LD$_{50}$ | D$_{95}$ |
| cypermethrin | 11.0 | 36.7 | 14.1 | 58.1 | 0.78 | 0.63 |
| transmix | 9.4 | 25.5 | 7.1 | 23.1 | 1.32 | 1.10 |
| chinmix | 4.6 | 21.9 | 3.5 | 16.8 | 1.31 | 1.30 |
| 1RcisS + 1RtransS$^x$ | 2.3 | 8.4 | 1.6 | 4.7 | 1.44 | 1.79 |

$^x$1:1 mixture

TABLE 3

Interaction of various cypermethrin isomer mixtures and quinalphos on house fly (*Musca domestica*) measured topically at different combination ratios

| dose (ng × fly$^{-1}$) | | measured activity (%) | | | expected activity (%) | cotoxicity index (%) |
|---|---|---|---|---|---|---|
| CIP | QUI$^x$ | CIP | QUI | CIP + QUI | | |
| | | | mortality | | | |

TABLE 3-continued

Interaction of various cypermethrin isomer mixtures and quinalphos on house fly (*Musca domestica*) measured topically at different combination ratios

| | | | | | | |
|---|---|---|---|---|---|---|
| 1:10 | | | | | | |
| 3.35 | 34 | 5 | 0 | 0 | 5 | −5 |
| 4.80 | 48 | 10 | 0 | 10 | 10 | 0 |
| 6.86 | 69 | 30 | 0 | 20 | 30 | −10 |
| 9.80 | 98 | 45 | 0 | 35 | 45 | −10 |
| 14.00 | 140 | 60 | 0 | 50 | 60 | −10 |
| 20.00 | 200 | 80 | 0 | 65 | 80 | −15 |
| 1:20 | | | | | | |
| 3.35 | 67 | 5 | 0 | 0 | 5 | −5 |
| 4.80 | 96 | 10 | 0 | 0 | 10 | −10 |
| 6.86 | 138 | 30 | 0 | 20 | 30 | −10 |
| 9.80 | 196 | 45 | 0 | 40 | 45 | −5 |
| 14.00 | 280 | 60 | 15 | 65 | 75 | −10 |
| 20.00 | 400 | 80 | 35 | 90 | 100 | −10 |

| CHX | QUI | CHX | QUI | CHX + QUI | | |
|---|---|---|---|---|---|---|
| 1:5 | | | | | | |
| 1.18 | 6 | 10 | 0 | 0 | 10 | −10 |
| 1.68 | 8 | 15 | 0 | 10 | 15 | −5 |
| 2.40 | 12 | 25 | 0 | 15 | 25 | −10 |
| 3.43 | 17 | 35 | 0 | 25 | 35 | −10 |
| 4.90 | 25 | 50 | 0 | 45 | 50 | −5 |
| 7.00 | 35 | 70 | 0 | 60 | 70 | −10 |
| 10.00 | 50 | 80 | 0 | 70 | 80 | −10 |
| 1:10 | | | | | | |
| 1.18 | 12 | 10 | 0 | 15 | 10 | −5 |
| 1.68 | 17 | 15 | 0 | 25 | 15 | −10 |
| 2.40 | 24 | 25 | 0 | 35 | 25 | +10 |
| 3.43 | 34 | 35 | 0 | 45 | 35 | −10 |
| 4.90 | 49 | 50 | 0 | 55 | 50 | −5 |
| 7.00 | 70 | 70 | 0 | 80 | 70 | +10 |
| 10.00 | 100 | 80 | 0 | 90 | 80 | +10 |
| 1:20 | | | | | | |
| 0.82 | 16 | 0 | 0 | 15 | 0 | −15 |
| 1.18 | 24 | 10 | 0 | 25 | 10 | +15 |
| 1.68 | 34 | 15 | 0 | 40 | 15 | +25 |
| 2.40 | 48 | 25 | 0 | 50 | 25 | +20 |
| 3.43 | 69 | 35 | 0 | 70 | 35 | +35 |
| 4.90 | 98 | 50 | 0 | 85 | 50 | +25 |
| 7.00 | 140 | 70 | 0 | 100 | 70 | +30 |
| 10.00 | 200 | 80 | 0 | 100 | 80 | +20 |

| 1RcisS + 1RtransS | QUI | 1RcisS + 1RtransS | QUI | 1RcisS + QUI 1RtransS | | |
|---|---|---|---|---|---|---|
| | | | | mortality | | |
| 1:10 | | | | | | |
| 0.82 | 8 | 5 | 0 | 15 | 5 | +10 |
| 1.18 | 12 | 20 | 0 | 35 | 20 | +15 |
| 1.68 | 17 | 35 | 0 | 50 | 35 | +15 |
| 2.40 | 24 | 55 | 0 | 70 | 55 | +25 |
| 3.43 | 34 | 70 | 0 | 90 | 70 | +20 |
| 4.90 | 49 | 80 | 0 | 100 | 80 | +20 |

| TRX | QUI | TRX | QUI | TRX + QUI | | |
|---|---|---|---|---|---|---|
| 1:10 | | | | | | |
| 3.43 | 34 | 5 | 0 | 15 | 5 | +10 |
| 4.90 | 49 | 15 | 0 | 35 | 15 | +20 |
| 7.0 | 70 | 30 | 0 | 45 | 30 | +15 |
| 10.0 | 100 | 55 | 0 | 70 | 55 | +15 |

*Quinalphos doses were rounded to intergers.

EXAMPLE 3

The interaction of chinmix and certain phosphate esters are examined by the method used in Example 1 and it shows that a synergistic activity can be observed when combining chinmix 1:10 or at a more extreme ratio of pyrethroid:phosphate ester with diazinone, triazophos, methidathion and heptenophos.

TABLE 5

Interaction of chinmix with various organic phosphate ester insecticides on house fly (*Musca domestica*) measured by topical methods

| dose (ng × fly$^{-1}$) | | measured activity (%) | | | expected activity (%) | cotoxicity index (%) |
|---|---|---|---|---|---|---|
| CHX | DIA | CHX | DIA | CHX + DIA | | |
| 1:10 | | | | | | |
| 0.57 | 6 | 0 | 0 | 5 | 0 | −5 |
| 0.82 | 8 | 0 | 0 | 10 | 0 | −10 |

TABLE 5-continued

Interaction of chinmix with various organic phosphate ester insecticides on house fly (*Musca domestica*) measured by topical methods

| | | | | | | |
|---|---|---|---|---|---|---|
| 1.18 | 12 | 0 | 0 | 20 | 0 | +20 |
| 1.88 | 19 | 5 | 0 | 25 | 5 | +20 |
| 2.40 | 24 | 10 | 0 | 40 | 10 | +30 |
| 3.43 | 34 | 25 | 0 | 50 | 25 | +25 |
| 4.90 | 49 | 45 | 0 | 70 | 45 | +25 |
| 7.00 | 70 | 70 | 0 | 90 | 70 | +20 |
| 10.00 | 100 | 85 | 0 | 100 | 85 | +15 |

| CHX | TRIA | CHX | TRIA | CHX + TRIA | | |
|---|---|---|---|---|---|---|
| 1:10 | | | | | | |
| 0.82 | 8 | 0 | 0 | 5 | 0 | +5 |
| 1.18 | 12 | 0 | 0 | 10 | 0 | +10 |
| 1.88 | 19 | 5 | 0 | 20 | 5 | +15 |
| 2.40 | 24 | 10 | 0 | 30 | 10 | +20 |
| 3.43 | 34 | 25 | 0 | 60 | 25 | +35 |
| 4.90 | 49 | 45 | 0 | 70 | 45 | +25 |
| 7.00 | 70 | 70 | 0 | 95 | 70 | +15 |
| 10.00 | 100 | 85 | 0 | 100 | 85 | +15 |
| 1:50 | | | | | | |
| 0.57 | 29 | 0 | 0 | 5 | 0 | +5 |
| 0.82 | 41 | 0 | 0 | 15 | 0 | +15 |
| 1.18 | 59 | 0 | 0 | 20 | 0 | +20 |
| 1.88 | 94 | 5 | 0 | 35 | 5 | +30 |
| 2.40 | 120 | 10 | 0 | 50 | 10 | +40 |
| 3.43 | 172 | 25 | 0 | 70 | 25 | +45 |
| 4.90 | 245 | 45 | 5 | 85 | 50 | +35 |
| 7.00 | 350 | 70 | 25 | 100 | 95 | +5 |
| 10.00 | 500 | 85 | 45 | 100 | 100 | — |

| CHX | MET | CHX | MET | CHX + MET | | |
|---|---|---|---|---|---|---|
| 1:10 | | | | | | |
| 0.82 | 8 | 0 | 0 | 5 | 0 | +5 |
| 1.18 | 12 | 0 | 0 | 10 | 0 | +10 |
| 1.88 | 19 | 5 | 0 | 30 | 5 | +25 |
| 2.40 | 24 | 10 | 0 | 50 | 10 | +40 |
| 3.43 | 34 | 25 | 0 | 65 | 25 | +40 |
| 4.90 | 49 | 45 | 0 | 70 | 45 | +25 |
| 7.00 | 70 | 70 | 0 | 90 | 70 | +20 |
| 10.00 | 100 | 85 | 0 | 100 | 85 | +15 |

| CHX | HEPT | CHX | HEPT | CHX + HEPT | | |
|---|---|---|---|---|---|---|
| 1:5 | | | | | | |
| 1.88 | 9 | 5 | 0 | 0 | 5 | −5 |
| 2.40 | 12 | 10 | 0 | 5 | 10 | −5 |
| 3.43 | 17 | 25 | 0 | 20 | 25 | −5 |
| 4.9 | 25 | 45 | 0 | 45 | 45 | 0 |
| 7.0 | 35 | 70 | 0 | 65 | 70 | −5 |
| 10.0 | 50 | 85 | 0 | 75 | 85 | −10 |
| 1:20 | | | | | | |
| 0.82 | 16 | 0 | 0 | 5 | 0 | +5 |
| 1.18 | 24 | 0 | 0 | 20 | 0 | +20 |
| 1.88 | 38 | 5 | 0 | 30 | 5 | +25 |
| 2.40 | 48 | 10 | 0 | 50 | 10 | +40 |
| 3.43 | 69 | 25 | 0 | 65 | 25 | +40 |
| 4.90 | 98 | 45 | 0 | 75 | 45 | +30 |
| 7.00 | 140 | 70 | 0 | 90 | 70 | +20 |
| 10.00 | 200 | 85 | 10 | 100 | 95 | +5 |

| CHX | MET | CHX | MET | CHX + MET | | |
|---|---|---|---|---|---|---|
| 1:20 | | | | | | |
| 0.57 | 11 | 0 | 0 | 0 | 0 | 0 |
| 0.82 | 16 | 0 | 0 | 5 | 0 | +5 |
| 1.18 | 24 | 0 | 0 | 20 | 0 | +20 |
| 1.88 | 38 | 5 | 0 | 35 | 5 | +30 |
| 2.40 | 48 | 10 | 0 | 60 | 10 | +50 |
| 3.43 | 69 | 25 | 0 | 70 | 25 | +45 |
| 4.90 | 98 | 45 | 0 | 85 | 45 | +40 |
| 7.00 | 140 | 70 | 0 | 100 | 70 | +30 |
| 10.00 | 200 | 85 | 10 | 100 | 95 | +5 |

EXAMPLE 4

The efficiency was determined on potato beetle (L. decemlineata) imagos collected from free land under similar technical conditions like in Example 1 and the results are summarized in Table 6.

TABLE 6

Efficiency of an insecticide mixture against potato beetle (*L. decemlineata*) imagos.
Ratio of pyrethroid:phosphate ester = 1:10

| dose (ng × fly$^{-1}$) | | measured activity (%) | | | expected activity (%) | cotoxicity index (%) |
|---|---|---|---|---|---|---|
| CHX | QUI | CHX | QUI | CHX + QUI | | |
| 50 | 500 | 80 | 10 | 100 | 90 | +10 |
| 25 | 250 | 60 | 0 | 75 | 60 | +15 |
| 12.5 | 125 | 40 | 0 | 60 | 40 | +20 |
| 6.25 | 62.5 | 20 | 0 | 35 | 20 | +15 |
| 3.125 | 31.25 | 10 | 0 | 20 | 10 | +10 |
| TRX | QUI | TRX | QUI | TRX + QUI | | |
| 50 | 500 | 65 | 10 | 35 | 75 | +10 |
| 25 | 250 | 30 | 0 | 60 | 30 | +30 |
| 12.5 | 125 | 0 | 0 | 25 | 0 | +25 |
| CHX | PHL | CHX | PHL | CHX + PHL | | |
| 50 | 500 | 80 | 0 | 95 | 80 | +15 |
| 25 | 250 | 60 | 0 | 70 | 60 | +10 |
| 12.5 | 125 | 40 | 0 | 55 | 40 | +15 |
| 6.25 | 62.5 | 20 | 0 | 30 | 20 | +10 |
| 3.125 | 31.25 | 10 | 0 | 15 | 10 | −5 |

EXAMPLE 5

The activity of piperonyl butoxide in various doses and chinmix and quinalphos at a ratio of 1:10 was examined as in Example 1 for insecticidal activity. The results are shown in the following table.

TABLE 7

Effect of piperonyl butoxide at different ratios on the insecticidal activity of a 1:10 mixture of chinmix and quinalphos on house fly (*Musca domestica*) measured topically

| dose (ng × fly$^{-1}$) | | measured activity (%)$^x$ | | | | increase of activity (%)$^x$ | | |
|---|---|---|---|---|---|---|---|---|
| CHX + QUI | | (1) | (2) | (3) | (4) | (2) | (3) | (4) |
| | | mortality | | | | | | |
| 1.18 + | 12 | 15 | 15 | 20 | 25 | +0 | +5 | +10 |
| 1.68 + | 17 | 25 | 30 | 35 | 40 | +5 | +10 | +15 |
| 2.40 + | 24 | 35 | 45 | 50 | 65 | +10 | +15 | +30 |
| 3.43 + | 34 | 45 | 65 | 70 | 75 | +20 | +25 | +30 |
| 4.90 + | 49 | 55 | 75 | 85 | 90 | +20 | +30 | +35 |
| 7.00 + | 70 | 80 | 90 | 95 | 100 | +10 | +15 | +20 |
| 10.00 + | 100 | 90 | 95 | 100 | 100 | +5 | +10 | +10 |

$^x$symbols:
(1) CXH + QUI neat
(2) CHX + QUI + PBO, CHX:PBO = 1:2
(3) CHX + QUI + PBO, CHX:PBO = 1:4
(4) CHX + QUI + PBO, CHX:PBO = 1:8

EXAMPLE 6

10 g of chinmix are dissolved in 475 g of xylene at 40° C. under stirring. Under further stirring 35 g of alkyl aryl sulphonate calcium salt are added to the solution, as well as a mixture of 80 g alkyl aryl phenol polyglycolether (10 EO). After complete dissolving 400 g of quinalphos in 50% xylene are added. The composition of the invention gives a stable emulsion after 24 hours in Cipac D water at a concentration of 0.2 percent by weight and 5 percent by weight.

EXAMPLE 7

To 80 g of xylene a calicum salt of 20 g alkyl aryl sulphonate and 90 g of tristiryl-phenolethoxylate (20 EO) are added at 40° C. 400 g of piperonyl butoxide are also added to the solution. 10 g of chinmix are slowly dissolved under stirring in the mixture. After complete dissolving under stirring a solution of 400 g quinalphos in 50% xylene is added. The composition according to the example remained a stable emulsion after 2 hours in Cipac D water at a concentration of 0.2, 1 and 5 percent by weight.

EXAMPLE 8

In 725 g Solvesso 100 10 g of alkyl aryl sulphonate calcium salt, and 55 g of alkyl phenol polyglycolether (10 EO) are dissolved. 200 g phosalon are added at 20° C. to the solution. The solution is heated to 40° C. and 10 g of chinmix are dissolved in the solution. In a water of hardness 342 and 34.2 ppm at a concentration of 0.5 and 4 percent by weight the stability of the emulsion was satisfactory at 20° C., 30° C. within 4 hours.

EXAMPLE 9

18 g of calcium salt of alkyl aryl sulphonate and 60 g of alkyl phenol polyglycol ether (10 EO) are dissolved in 512 g Solvesso 150. 400 g of phosalon are added to the solution at room temperature and 10 g of chinmix are dissolved at 40° C. and added. The composition gave a stable emulsion when examined for 2 hours in Cipac D water at a concentration of 0.2%.

EXAMPLE 10

20 g of calcium salt of alkyl aryl sulphonate, 70 g of alkyl phenol polyglycol ether (10 EO) and 10 g of tristiryl phenolethoxylate (20 EO) are dissolved in 440 g of Aromatol (aromatic solvent mixture). 200 g of phosalone are added at 20° C. to the solution. 250 g of piperonyl butoxide are added to the mixture under stirring. 10 g of chinmix are added under slow stirring at 40° C. The stability of the emulsion was determined by Cipac method and it shows that a stable emulsion is obtained.

EXAMPLE 11

15 g of calcium salt of alkyl aryl sulphonate, 20 g of alkyl phenyl polyglycol ether (15 EO), 70 g of tristiryl phenolethoxylate (20 EO) are dissolved in 85 g of Aromatol (aromatic solvent mixture). 400 g of piperonyl butoxide are added to the solution. 400 g of phosalon are added to the mixture at 40° C. followed by the addition of 10 g of chinmix. A stable emulsion is obtained in Cipac D water at concentrations of 0.2, 1, 5% after 30 minutes and 2 hours.

EXAMPLE 12

10 g calcium salt of alkyl aryl sulphonate, 60 g alkyl phenol polyglycol ether (15 EO), 20 g of tristiryl phenolethoxylate (20 EO) are added to 400 g of quinalphos dissolved in 50% xylene. Under slow stirring 10 g of chinmix are dissolved at 40° C. After dissolving 400 g of piperonyl butoxide are added. 20 g n-butanol and 80 g water are added under further stirring. The stability of the emulsion from the transparent solution measured by Cipac method was suitable.

EXAMPLE 13

200 g piperonyl butoxide and 60 g Solvesso 100 were admixed. 150 g tristiryl phenolethoxylate (20 EO), 15 g alkyl phenol polyglycol ether (8 EO) and 5 g calcium salt of alkyl aryl sulphonate are added to the mixture. 200 g of phosalone are added at 20° C. followed by dissolving 10 g of chinmix in the solution at 40° C. The solution is cooled to 20° C. and a mixture of 50 g n-butanol and 300 g of water is added. A stable emulsion is obtained from the transparent solution in Cipac D water for 14 hours at concentrations of 0.2 and 1 percent by weight.

EXAMPLE 14

5 g of chinmix are dissolved in 200 g quinalphos in 50% xylene. To a laboratory fluidization drier 450 g Wessalon S (synthetic silicic acid of great specific surface) are added. A 2 layered pulveriser is placed in the fluid bed of the fluidization drier. At an input temperature of 80° C. on the fluidized Wessalon S a xylene solution of quinalphoschinmix is pulverized at a flow rate of 300 ml/hour. When terminating the pulverization, xylene is removed from Wessalon S in warm air stream. After drying the mixture of chinmix and quinalphos applied on the Wessalon S carrier the mixture is poured into a laboratory powder homogenizator of 3 l capacity. 320 g of neuburg chalk, 60 g Dispersogen A (a condense product of naphthalene sulphonic acid with formaldehyde) and 20 g Netzer IS (sodium salt of aliphatic sulphonic acid) were added in the given order under stirring. When the addition of all the components is completed homogenization is continued for 20 sec. The powder mixture is ground in an air mill to a particle size of 10 $\mu$m. Floatability according to CIPAC: 86%. Moisturization time: 20 sec.

EXAMPLE 15

In 100 g 50% xylene quinalphos solution 5 g of chinmix are dissolved. The xylene solution is pulverized on 400 g Wessalon S carrier by fluidization process disclosed in Example 1. The dry mixture is poured into a laboratory homogenizer described in Example 1, whereafter 465 g of neuburg chalk, 60 g of Dispersogen A and 20 g of Netzer IS are homogenized. The obtained powder mixture is ground in an airmill to a particle size of less than 10 $\mu$m. Floatability according to CIPAC: 82%. Moisturization time: 18 days.

EXAMPLE 16

In 100 g of 50% xylene quinalphos solution 100 g of piperonyl butoxide are dissolved. 5 g of chinmix are added to the solution and the mixture is stirred until complete Wessalon S carrier and it is dried. The dry premix is plaaced into a laboratory homogenizer and under stirring 195 g of neuburg chalk, 70 g of Dispersogen A and 30 g of Netzer IS are added. The homogeneous product is ground in an air mill. Floatability of the product according to CIPAC: 85%. Moisturization time: 22 days.

EXAMPLE 17

100 g of 50% xylene quinalphos solution 50 g of piperonyl butoxide are dissolved. 5 g of chinmix are added under stirring and stirring is continued for complete dissolution. The xylene solution is applied on 400 g of Wessalon S carrier in a fluidization drying apparatus as described in Example 1 and dried. The dry powder mixture is supplemented with 395 g neuburg chalk, 70 g of Dispersogen A and 30 g of Netzer IS in a laboratory homogenizer. The product is ground. Floatability according to CIPAC: 83%. Moisturization time: 22 days.

EXAMPLE 18

5 g of chinmix are dissolved in 150 ml of a 1:1 xylene chloroform mixture. 100 g of phosalone are added. The solution is pulverized on 400 g of Wessalon S by fluidization given in Example 1, followed by removing xylene and chloroform by drying. The dry powder mixture is supplemented in a laboratory homogenizer with 250 g neuburg chalk, 70 g of sodium lignine sulphonate and 25 g of Atlox 4995 (ethoxylated alkyl ether) and the homogeneous powder mixture is ground in an air mill to a particle size less than 10 $\mu$m. The obtained product's floatability according to CIPAC: 95%. Moisturization time: 7 sec.

EXAMPLE 19

5 g of chinmix and 50 g phosalone are dissolved in 75 ml of xylene-chloroform mixture according to Example 5. After complete dissolution the solution is applied on 400 g Wessalon S carrier in a fluidization apparatus and dried. The dried powder mixture is supplemented in a laboratory homogenizer with 390 g neuburg chalk, 60 g of sodium salt of lignine sulphonate and 20 g Atlos 4995. The powder mixture is ground after complete homogenization in an air mill. Floatability according to CIPAC: 95%. Moisturization time: 15 sec.

EXAMPLE 20

In 100 ml of a xylene and chloroform mixture according to Example 5, 5 g of chinmix, 100 g of piperonyl butoxide, 50 g of phosalone are dissolved. The above solution is applied to 450 g Wessalon S by fluidization process according to Example 1 and the solvent is removed by drying. The dry mixture is supplemented with 190 g neuburg chalk, 75 g of sodium salt of lignine sulphonate and 30 g of Atlox 4873 (ethoxylated alkyl ether) in a laboratory powder homogenizer. The homogeneous powder mixture is ground in an air mill. The obtained product's floatability according to CIPAC: 86%. Moisturization time: 18 sec.

EXAMPLE 21

In 100 ml of xylene and chloroform mixture according to Example 5 5 g of chinmix, 50 g of piperonyl butoxide, 50 g of phosalone are dissolved. The above solution is applied to 400 g Wessalon S by fluidization process according to Example 1 and the solvent is removed by drying. The dry mixture is supplemented with 305 g neuburg chalk, 65 g of sodium salt of lignine sulphonate and 25 g of Atlox 4873 (ethoxylated alkyl ether) in a laboratory powder homogenizer. The homogeneous powder mixture is ground in an air mill. The obtained product's floatability according to CIPAC: 89%. Moisturization time: 19 sec.

We claim:

1. A multicomponent pesticidal composition against arthropods containing as active ingredient pyrethroids and phosphate esters comprising as a sole cypermethrin component out of the 8 possible isomers, one of the following cypermethrin isomers or cypermethrin isomer mixtures:
   1RcisS;
   1RtransS;
   1ScisR;
   1StransR;
   1RcisS and 1RtransS in a 1:1 weight mixture;
   1RcisS+1ScisR:1RtransS+1StransR in a 40:60 weight mixture; or
   1RtransS+1StransR in a 50:50 weight mixture; and as a second component a compound selected from the group consisting of diazinon, triazophos, methidathion, heptenophos, phosalone, and quinalphos, wherein the weight ratio of the cypermethrin component to the second component is 1:10 to 1:40.

2. A multicomponent pesticidal composition against arthropods containing as active ingredient pyrethroids and phosphate esters comprising as a sole cypermethrin component out of the 8 possible isomers, one of the following cypermethrin isomers or cypermethrin isomer mixtures:
   1RcisS;
   1RtransS;
   1ScisR;
   1StransR;
   1RcisS and 1RtransS in a 1:1 weight mixture;
   1RcisS+1ScisR:1RtransS+1StransR in a 40:60 weight mixture; or
   1RtransS+1StransR in a 50:50 weight mixture; and as a second component quinalphos, wherein the weight ratio of the cypermethrin component to the second component is 1:10 to 1:20.

3. A multicomponent pesticidal composition against arthropods containing as active ingredient pyrethroids and phosphate esters comprising as a sole cypermethrin component out of the 8 possible isomers, the following cypermethrin isomer mixture:
   1RcisS+1ScisR:1RtransS+1StransR in a 40:60 weight mixture;
   and as a second component a compound selected from the group consisting of diazinon, triazophos, methidathion, heptenophos, phosalone and quinalphos, wherein the weight ratio of the cypermethrin component to the second component is 1:10 to 1:20.

4. A multicomponent pesticidal composition against arthropods containing as active ingredient pyrethroids and phosphate esters comprising as a sole cypermethrin component out of the 8 possible isomers, the following cypermethrin isomer mixture:
   1RcisS+1ScisR:1RtransS+1StransR in a 40:60 weight mixture;
   and as a second component quinalphos, wherein the weight ratio of the cypermethrin component to the second component is 1:10 to 1:20.

* * * * *